United States Patent
Fumex et al.

(10) Patent No.: US 10,219,850 B2
(45) Date of Patent: Mar. 5, 2019

(54) OSTEOSYNTHESIS SCREW

(71) Applicants: Laurent Fumex, Madison, CT (US);
Thierry Masseglia, La Garde (FR)

(72) Inventors: Laurent Fumex, Madison, CT (US);
Thierry Masseglia, La Garde (FR)

(*) Notice: Subject to any disclaimer, the term of this patent is extended or adjusted under 35 U.S.C. 154(b) by 150 days.

(21) Appl. No.: 14/903,082

(22) PCT Filed: Jul. 2, 2014

(86) PCT No.: PCT/FR2014/051694
§ 371 (c)(1),
(2) Date: Jan. 6, 2016

(87) PCT Pub. No.: WO2015/007975
PCT Pub. Date: Jan. 22, 2015

(65) Prior Publication Data
US 2016/0183993 A1    Jun. 30, 2016

(30) Foreign Application Priority Data
Jul. 18, 2013  (FR) ...................................... 13 57084

(51) Int. Cl.
*A61B 17/86* (2006.01)
*A61B 17/84* (2006.01)
*A61B 17/68* (2006.01)

(52) U.S. Cl.
CPC ............ *A61B 17/863* (2013.01); *A61B 17/84* (2013.01); *A61B 17/864* (2013.01); *A61B 17/8685* (2013.01); *A61B 2017/681* (2013.01)

(58) Field of Classification Search
CPC ..... A61B 17/86; A61B 17/863; A61B 17/864; A61B 17/8685
See application file for complete search history.

(56) References Cited

U.S. PATENT DOCUMENTS

| | | | |
|---|---|---|---|
| 4,640,271 A * | 2/1987 | Lower ............... | A61B 17/8685 606/105 |
| 5,743,912 A | 4/1998 | Lahille et al. | |
| 2011/0295252 A1* | 12/2011 | Tipirneni ............ | A61B 17/683 606/62 |

FOREIGN PATENT DOCUMENTS

WO          9109572          7/1991

OTHER PUBLICATIONS

Search Report dated 2014.

* cited by examiner

*Primary Examiner* — Christopher Beccia
(74) *Attorney, Agent, or Firm* — Ipsilon USA, LLP

(57) ABSTRACT

The invention relates to an osteosynthesis device intended for holding, distraction or compression of fragments of a fractured bone. The device comprises a threaded pin (1) having a threaded head (2) at its distal end, and a ring (4) adapted to slide on the threaded pin (1). The pin (1) and the ring (4) are made of materials allowing them to be cut. The ring (4) has at its distal end a threaded head (5) whose diameter is at least equal to the diameter of the threaded head (2) of the pin (1). The threaded pin (1) and the threaded ring (4) are hollow so as to allow them to be crimped during the cutting.

9 Claims, 2 Drawing Sheets

OSTEOSYNTHESIS SCREW

RELATED APPLICATIONS

This application is a National Phase Application of PCT/FR2014/051694, filed on Jul. 2, 2014, which in turn claims the benefit of priority from French Patent Application No. 13 57084 filed on Jul. 18, 2013, the entirety of which are incorporated herein by reference.

BACKGROUND

Field of the Invention

The present invention relates to an osteosynthesis device intended for holding, distraction or compression of fragments of a fractured bone.

Description of Related Art

Numerous devices of the osteosynthesis screw type are known, threaded or unthreaded pin, staple, screw or pin locking in a plate, making it possible to carry out osteosynthesis of a fractured bone.

U.S. Pat. No. 7,037,309 describes a hollow self-tapping screw with two screw threads having different pitches, which makes it possible to compress a fractured bone. The principle of this screw is that the difference between the pitch of the distal screw thread and the pitch of the proximal screw thread allows compression of the bone when the screw is screwed. However, the value of the compression is not controllable because it depends on the reduction quality of the fracture focus as well as on the quality of the bone. Furthermore, a wide range of screws is necessary in order to satisfy the different lengths of fractured bones.

Patent US20110218580 describes a screw with two screw threads having different pitches, the threaded head of which locks in a plate. This device makes it possible to hold a fraction, but it cannot be implanted in the bone.

U.S. Pat. No. 7,641,677 describes a threaded pin having a ring which is screwed onto the screw thread of the pin. This device allows holding and compression of the fractured bone fragment, but it cannot be implanted.

Patent WO2009/103886 describes a threaded pin which passes through a bush which, while being locked in a plate, blocks the pin in translation. This device makes it possible to hold a fracture, but it cannot be implanted in the bone.

These devices effectively allow holding and/or compression of the fragments of a fractured bone. They do not, however, allow the practitioner the choice of retracting, compressing or holding a bone fragment, depending on the type of fracture.

Objects and Summary

The object of the present invention is to provide a device which allows the practitioner manual adjustment of the distraction or compression, and holding of a bone fragment, and which can be implanted in the bone, makes it possible to reduce significantly the range of implants, and allows fitting by means of conventional tools.

The osteosynthesis device according to the invention, which may be used in particular for fractures of the small bones and is intended for holding, distraction or compression of fragments of a fractured bone, comprises a threaded pin having a threaded head at its distal end, and a ring adapted to slide on the threaded pin. The pin and the ring are made of materials allowing them to be cut. The ring has at its distal end a threaded head whose diameter is at least equal to the diameter of the threaded head of the pin. The threaded pin and the threaded ring are hollow so as to allow them to be crimped during the cutting.

Preferably, the threaded pin is entirely hollow.

According to one variant, the threaded pin is solid at the threaded head.

Advantageously, the pin and the ring are made of deformable biocompatible materials. One example of such a material is stainless steel of the type 316LVM, which may be cold-hammered for the pin, so as to have a tensile strength Rm of more than 900 MPa, and overhardened for the ring, with Rm≈600 MPa.

Preferably, the screw threads of the threaded heads are identical.

According to one variant, the screw threads of the threaded heads are different.

Advantageously, during the cutting, the cross sections of the pin and of the ring are deformed in such a way that in a plane perpendicular to the axes of the pin and of the ring, their edges are moved toward one another in a first direction and are moved away from one another in a second direction, which is perpendicular to the first direction.

According to the invention, the threaded pin has a cylindrical body ending in a distal external screw thread of the bone type. The threaded pin may be entirely hollow so that it can be guided on the pin, or partially hollow in order to be screwed directly. The distal external screw thread of the pin has known means which promote self-tapping. The threaded ring has a cylindrical body ending in a distal external screw thread of the bone type, and is entirely hollowed in order to slide on the cylindrical body of the threaded pin. The distal external screw thread of the ring has known means which promote self-tapping.

According to an advantageous embodiment of the invention, the length of the distal external screw threads is approximately 5 mm.

The advantages of the present invention will become clearer with the following fitting explanation. Using a motor or manually with the aid of a "Jacob" mandrel, the practitioner inserts the partially hollow threaded pin through the proximal bone fragment until the distal screw thread of the threaded pin is anchored in the distal bone. After having disconnected the drive means from the cylindrical body of the partially hollow threaded ring, he slides the threaded pin over the cylindrical body of the partially hollow threaded pin until bone contact, then screws it into the bone. At this moment, by pulling or pushing on the body of the threaded ring, he can either move the proximal bone fragment away from the distal bone or compress the bone fragment onto the bone. When the desired distraction or compression has been carried out, while holding the arrangement in place, the practitioner cuts the assembly level with the bone, for example by means of cutting pliers. The cutting pliers, acting on these two hollow pieces, deform the cross sections of the bodies of the pin and of the ring before cutting them, thus crimping the hollow cylindrical body of the threaded pin into the hollow cylindrical body of the threaded ring. This crimping makes it possible to hold the arrangement in the position achieved by the practitioner.

The embodiment according to which the threaded pin is entirely hollow allows the practitioner to fit it by means of a guide pin of "Kirschner" type, which is inserted beforehand and on which the threaded pin can slide. When the entirely hollow threaded pin is anchored in the distal bone, the practitioner withdraws the "Kirschner" pin and continues his manipulation as described above.

It will be understood that the device according to the present invention operates in the same way whether the bone fragment is distal relative to a proximal bone, or in order to secure two or more bone fragments.

Extraction of the device is particularly simple. During the crimping, the hollow cylindrical body of the threaded pin and the body of the threaded ring deform in such a way as to leave a slot making it possible to introduce a drive tool, such as the end of a screwdriver, which drives the two pieces during unscrewing.

BRIEF DESCRIPTION OF THE DRAWINGS

Other characteristics and advantages of the present invention will become apparent from the following description, which relates to a preferred embodiment, with reference to the appended drawings in which.

DETAILED DESCRIPTION

Figure 1:
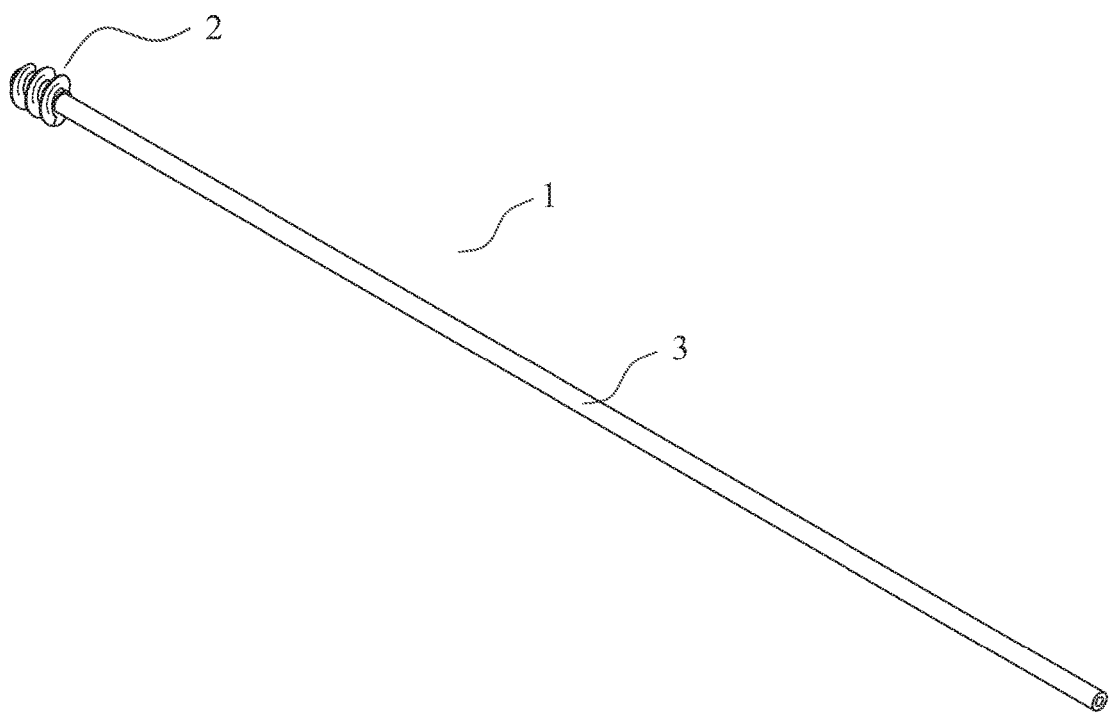
FIG. 1 represents a perspective view of a partially hollow threaded pin of a device according to the invention.

The threaded pin 1 represented in FIG. 1 is composed of a head 2 extended by a body 3. The head 2 is threaded with a known bone screw thread, the distal end of which may be of pyramidal shape and/or have means which promote tapping. The body 3 is hollow, and the head 2 is solid.

As an alternative, the threaded pin 1 may be entirely hollow in order to be guided on a pin positioned beforehand.

Figure 2:
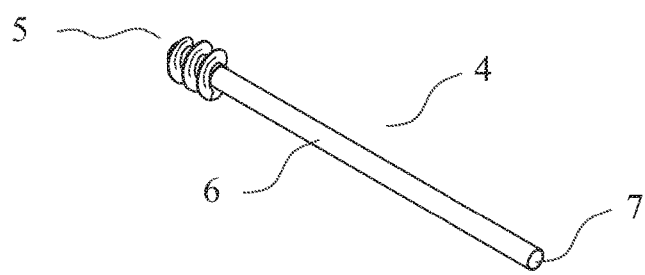
FIG. 2 represents a perspective view of the entirely hollow threaded ring of the device according to the invention.

The threaded ring 4 represented in FIG. 2 has a head 5 extended by a body 6. The head 5 is threaded with a known bone screw thread, the distal end of which may have means which promote tapping. The screw thread of the head 5 of the ring 4 is preferably identical to the screw thread of the head 2 of the pin 1, so that it can be screwed easily into the tapping carried out by the insertion of the threaded pin 1. The threaded ring 4 is entirely hollow so that it can slide on the body 3 of the pin 1. The bore 7 of the body 6 of the ring 4 has a diameter slightly greater than the external diameter of the body 3 of the pin 1.

According to one variant, the screw thread of the head 2 of the pin 1 is different from that of the head 5 of the ring 4. This is particularly advantageous in the case in which the bones or bone fragments in which the heads are anchored are of different types. For example, the pin may be fixed in a cortical bone and the ring in a spongy bone, or vice versa.

Depending on the variant, the diameter of the screw thread of the head 5 of the ring 4 may be greater than or equal to the diameter of the screw thread of the head 2 of the pin 1. Thus, the head 5 of the ring 4 does not have any play in the bone.

Figure 3:
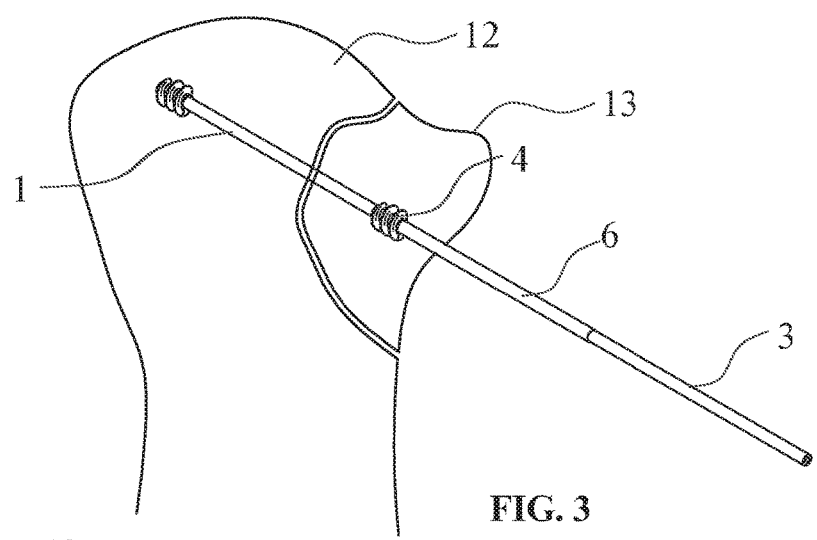
FIG. 3 represents a perspective view of the device according to the invention screwed into a bone, before compression.

FIG. 3 represents the device, composed of the pin 1 and the ring 4, screwed into a bone 12 whose fracture has not been reduced. The threaded pin 1 is screwed into the bone, and the body 3 of the pin 1 extends beyond the body 6 of the threaded ring 4 in order to facilitate handling. The threaded ring 4 is screwed into the bone fragment 13, and the body 6 of the ring 4 extends beyond the bone fragment 13 in order to facilitate handling.

Figure 4:
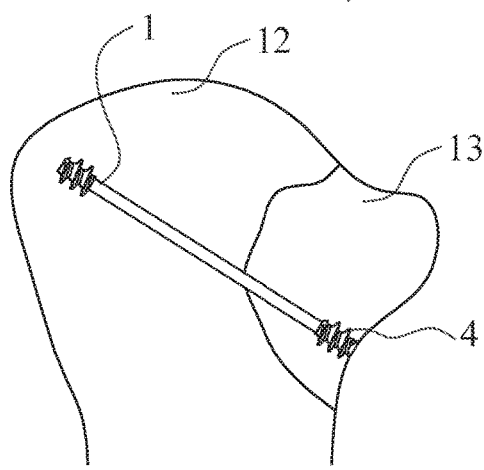
FIG. 4 represents a sectional view of the device according to the invention, screwed into a bone, after compression and cutting.

FIG. 4 represents the device after reduction of the fracture of the bone fragment 13 and cutting of the device level with the bone fragment 13. The cutting may, for example, be carried out with the aid of cutting pliers. Under the effect of the flush cutting pliers, before cutting, the body 3 of the pin 1 and the body 6 of the ring 4 are deformed, leading to crimping of the two bodies 3, 6.

Figure 5:
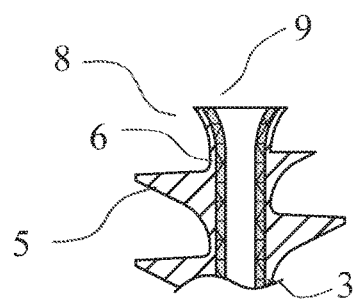
FIGS. 5 to 6 represent views illustrating the crimping of the device after cutting.

FIG. 5 represents a cross section, in a given plane containing the axes of the pin 1 and of the ring 4, of the threaded ring 4 and of a part of the body 3 of the pin 1 after cutting. The body 6 of the ring 4 is flared according to the shape 8, and the body 3 of the pin 1 is flared according to the shape 9. The combination of these two flared shapes makes it possible to block the body 3 of the pin 1 in translation toward the inside of the body 6 of the ring 4, and to block the threaded pin 1 in translation relative to the threaded ring 4.

Figure 6:
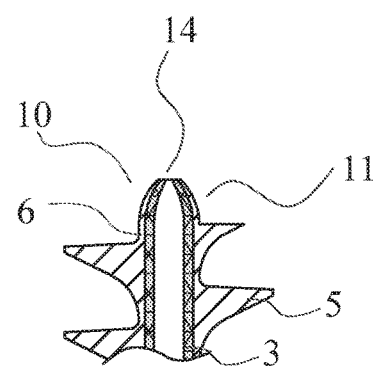

FIG. 6 represents a cross section, in a plane perpendicular to the plane of FIG. 5, of the threaded ring 4 and of a part of the body 3 of the pin 1 after cutting. The body 6 of the ring 4 is closed according to the shape 10, and the body 3 of the pin 1 is closed according to the shape 11. The combination of these two closed shapes makes it possible to block the body 3 of the pin 1 in translation toward the outside of the body 6 of the ring 4, and to block the threaded pin 1 in rotation relative to the threaded ring 4.

Thus, the deformations of the bodies 3, 6 of the pin 1 and of the ring 4, described with reference to FIGS. 5 and 6, block the threaded pin 1 in translation and in rotation relative to the threaded ring 4. The space 14 created during the cutting of the device by the edges of the two bodies 3, 6, which can be seen in FIG. 6, makes it possible to screw or unscrew the assembly by means of a screwdriver. For example, the practitioner may implant the assembly in the bone or alternatively extract it.

The invention claimed is:

1. Osteosynthesis device intended for holding, distraction or compression of fragments of a fractured bone, comprising:
    a threaded pin having a threaded head at its distal end, and
    a ring adapted to slide on the threaded pin,
in which the pin and the ring are made of materials allowing them to be cut, wherein:
    the ring has at its distal end a threaded head whose diameter is at least equal to the diameter of the threaded head of the pin, and
    the threaded pin and the threaded ring are hollow so as to allow them to be crimped during the cutting,
    the threaded pin and the threaded ring have a configuration which provides crimping of the threaded pin and the threaded ring by cutting both of them together.

2. Device according to claim 1, wherein the threaded pin is entirely hollow.

3. Device according to claim 1, wherein the threaded pin is solid at the threaded head.

4. Device according to one of claim 1, wherein the pin and the ring are made of deformable biocompatible materials.

5. Device according to claim 1, wherein the screw threads of the threaded heads are identical.

6. Device according to claim 1, wherein the screw threads of the threaded heads are different.

7. Device according to claim 1, wherein, during the cutting, the cross sections of the pin and of the ring are deformed in such a way that, in a plane perpendicular to the axes of the pin and of the ring, their edges are moved toward one another in a first direction and are moved away from one another in a second direction, which is perpendicular to the first direction.

8. Device according to claim 1, wherein the length of each of the screw threads is 5 mm.

9. Method for performing an osteosynthesis for holding, distraction or compression of fragments of a fractured bone, comprising:

provding an osteosynthesis device intended for holding, distraction or compression of fragments of a fractured bone, comprising:

a threaded pin having a threaded head at its distal end, and a ring adapted to slide on the threaded pin, in which the pin and the ring are made of materials allowing them to be cut, wherein:

the ring has at its distal end a threaded head whose diameter is at least equal to the diameter of the threaded head of the pin, and the threaded pin and the threaded ring are hollow so as to allow them to be crimped during the cutting, the threaded pin and the threaded ring have a configuration which provides crimping of the threaded pin and the threaded ring by cutting both of them together, inserting a hollow threaded pin through a proximal bone fragment to anchor it in the fractured bone, sliding the threaded pin over threaded pin, screwing the threaded pin into the bone fragment, carrying out a holding, distraction or compression operation of the fractured bone with the bone fragment, cutting both of the threaded pin and the threaded ring together to crimp both of them for holding the arrangement in position.

* * * * *